United States Patent [19]

Morre et al.

[11] 4,115,062

[45] Sep. 19, 1978

[54] CANCER DETECTION BY SERUM ANALYSIS OF GLYCOLIPIDS

[75] Inventors: D. James Morre, West Lafayette; Thomas M. Kloppel, Lafayette; Thomas W. Keenan, West Lafayette, all of Ind.

[73] Assignee: Purdue Research Foundation, West Lafayette, Ind.

[21] Appl. No.: 805,691

[22] Filed: Jun. 13, 1977

[51] Int. Cl.$^2$ ............................................. G01N 33/16
[52] U.S. Cl. ...................................... 23/230 B; 424/12
[58] Field of Search ......................... 23/230 B; 424/12

[56] References Cited

U.S. PATENT DOCUMENTS

| | | | |
|---|---|---|---|
| B 554,039 | 2/1976 | Grosser et al. | 424/12 X |
| 3,087,862 | 4/1963 | Penn | 424/12 |
| 4,043,757 | 8/1977 | Wagstaff | 23/230 B |

Primary Examiner—Robert M. Reese
Attorney, Agent, or Firm—John R. Nesbitt

[57] ABSTRACT

In humans and experimental animals, serum levels of sialic acid-containing glycolipids are elevated 1.5 to 3 fold. A method is described whereby the ganglioside content is estimated on as little as 0.5 ml of serum or plasma. The procedure permits, based on the analysis of a single biochemical parameter, cancer detection applicable to a wide range of human and animal tumor types.

11 Claims, No Drawings

CANCER DETECTION BY SERUM ANALYSIS OF GLYCOLIPIDS

BACKGROUND OF THE INVENTION

A priority objective of the National Cancer Program is the requirement for biochemical and/or immunological methods for early detection of cancer based on analysis of exfoliated cells or body fluids obtained from apparently normal individuals. This invention pertains to a biochemical method of cancer detection based on serum analysis of glycolipids.

Buck et al., Science 172, 169 (1971) first reported that tumor-characteristic sialofucosyl glycopeptides, present only in trace amounts in normal cells, are considerably elevated in tumor cells. Subsequently, glycopeptide alterations have been demonstrated in tumor cells obtained from peripheral blood of patients with active leukemia by VanBeek et al., Nature 253, 457 (1975). Sialic acid-containing glycosphingolipids termed gangliosides, are also altered in the direction of increased amounts of sialic acid as reviewed by Richardson et al., Biochem. Biophys. Acta 417, 55 (1975). These studies, however, were restricted to the tumor tissues themselves, and except for detection of leukemic cells, have had little or no diagnostic applications.

More recent studies from our laboratory at Purdue University (Merritt et al., manuscript to be published in J. Natl. Cancer Inst.) show that both gangliosides and ganglioside biosynthetic enzymes are elevated in tissues surrounding tumors as well as in the tumors themselves. These studies subsequently led to a study to determine if glycolipids were also elevated in the sera of animal models. In mice bearing transplantable mammary carcinomas, serum levels of sialic acid-containing glycolipids were found to be elevated 1.5 to 3 fold on pooled serum samples from which gangliosides were purified by column chromatography by Kloppel et al., *Proc. Nat. Acad. Sci. U.S.A.*, (to be published). An elevated and altered ganglioside pattern for pooled serum samples of Morris hepatoma-bearing rats published by Skipski et al., *Biochem. Biophys. Res. Commun.*, 67, 1122 (1975) showed an altered pattern in serum corresponding to that of the tumor tissue. These studies, however, employed standard methods of ganglioside extraction, purification, and quantification on pooled serum samples. The methods are tedious, time consuming, and not well adapted to routine clinical usage.

If sialic acid levels are to have diagnostic implications, it is essential that serum from individuals be analyzed. To accomplish the latter, a simplified extraction and purification procedure was employed that permitted analyses of 0.5 to 1.0 ml serum.

SUMMARY OF THE INVENTION

We have discovered that tumor bearing animal models, and human carcinoma patients, have elevated serum levels of glycolipid-bound sialic acid, that the glycolipid-bound sialic acid can be detected on samples of as little as 0.5 to 1.0 ml of serum or plasma, and that the procedure has diagnostic value as the basis for a biochemical method for early detection of cancer.

DETAILED DESCRIPTION OF THE INVENTION

Materials and Methods

Experimental animals and tumors. The tumor used was a transplantable mammary carcinoma, designated ST II, which originated spontaneously in a retired breeding female of the mouse strain $C_3H/HeJ$. The tumor was propagated by subcutaneous implantation of tumor fragments to male or female syngeneic recipients. Age matched controls of the same strain were injected with an equivalent amount of saline but received no tumor implant and were otherwise treated exactly as the principals. Tumor masses were examined for degree of vascularization, excised and weighed.

Determination of gangliosides. Groups of 25 carcinoma-bearing mice were exsanguinated 60 days after implantation of tumor fragments. Sera were pooled following centrifugation. Gangliosides were extracted with chloroform-methanol and further purified by chromatography on DEAE-Sephadex and Unisil silicic acid. Sialic acid assays were on purified gangliosides.

Individual mice bearing tumors were exsanguinated at 3 to 90 days after implantation of tumor fragments along with age and litter-matched control mice as described above. The sera (0.5–1 ml) obtained following centrifugation were extracted with chloroform-methanol (1:1) overnight. The extracts were filtered and the residue was extracted a second time with chloroform-methanol (2:1) overnight. The combined extracts were concentrated by evaporation and adjusted to 3 ml. To precipitate sialic acid-containing lipo- and glycoproteins (not elevated in sera of tumor bearers), 100 μl of a 0.1% solution of tripotassium citrate was added and the resulting precipitate removed by centrifugation. The post-citrate supernatant was analyzed for sialic acid using values calculated by the Warren (Warren, J. Biol. Chem. 234, 1971, 1959) formula to correct for variation due to unspecific absorbance.

Results

Animal model. The level of total ganglioside, based on determinations of sialic acid, was elevated about 2.5 times that of control values in sera of both male and female recipient mice carrying a transplantable mammary carcinoma of spontaneous origin, as shown in the following Table I:

TABLE I

Levels of ganglioside-bound sialic acid in pooled samples of sera from tumor-bearing mice sixty days post-transplant.

| Group | Sex | Sialic acid* (nanomoles/ml serum) | Ratio (experimental/control) |
|---|---|---|---|
| Control | Male | 14.7 | |
| | Female | 16.0 | |
| Tumor-bearing | Male | 32.6 | 2.21 |
| | Female | 42.4 | 2.65 |

*Gangliosides were extracted and purified by column chromatography from pooled sera of 25 mice prior to determination of ganglioside sialic acid.

Similar elevations were observed at 11, 21 and 35 days post-transplantation; at 11 days palpable tumor masses were not detected. These increases were not reflected by whole serum sialic acid or by sialic acid content of precipitated lipoproteins and glycoproteins which account for more than 90% of the sialic acid of the serum.

If sialic acid levels are to have diagnostic implications, it is essential that serum from individual animals be analyzed. To accomplish the latter, a simplified extraction and purification procedure was employed that permitted analyses of 0.5–1 ml of serum. When analyzed in this manner, all tumor-bearing mice had elevated serum levels of sialic acid when compared with age- and litter-matched controls, as shown in the following Table II:

TABLE II

Lipid-soluble sialic acid in sera from individual male mice bearing transplantable mammary carcinomas.

| Degree of vascularization* | Tumor mass (g) | Sialic acid (nanomoles per ml serum) | Ratio (experimental/control) |
|---|---|---|---|
| Low | 0.51 | 29 | 1.5 |
|  | 0.98 | 44 | 2.2 |
|  | 2.00 | 27 | 1.3 |
|  | 3.20 | 34 | 1.7 |
|  | 3.25 | 50 | 2.5 |
|  | 5.20 | 61 | 3.0 |
| High | 5.10 | 35 | 1.7 |
|  | 5.45 | 64 | 3.2 |
|  | 6.00 | 31 | 1.5 |
|  | 8.00 | 39 | 1.9 |
|  | 8.80 | 43 | 2.1 |
|  | 9.40 | 53 | 2.7 |

*Subjectively judged from number and size of prominent blood vessels associated with the tumor mass.

Gangliosides were determined on lipid extracts following precipitation of lipo- and glycoproteins by the citrate procedure for sera eight weeks after transplantation. Experimental values are averages from duplicate assays on 0.5 ml serum. Average control value for four mice was 20 ± 4 nanomoles sialic acid per ml serum. All individual experimental values were significantly different from controls using a 99% confidence interval.

The degree of elevation varied among individuals from 40% to 230% but each was statistically significant from controls at the 99% confidence interval. Near-quantitative extraction of gangliosides by the simplified method was shown from time course extraction studies, recovery of known amounts of purified gangliosides, and comparisons with standard chloroform-methanol extraction procedures (compare Tables I and II).

Determinations similar to those of Table II were conducted using the erythrocyte plug which formed after centrifugation of individual serum samples. This was carried out on the expectation that some proportion of the glycolipids of the serum might absorb to the erythrocyte membrane. There was, however, no increase in the level of glycolipid sialic acid of the erythrocytes that could be detected. Both control and tumor-bearing sera averaged 150 nmoles/gram wet weight of red blood cells.

Time course studies showed that sialic acid levels were elevated after 10–15 days for a fast-growing tumor of spontaneous origin and after about 20 days for a slower growing transplantable 7.12-dimethylbenz[a]anthracene-induced tumor. In both systems, tumor burdens of less than 0.5 g appeared capable of eliciting the ganglioside increase. On day 47, tumors were removed from 8 mice and the animals were sacrified 1, 2, 5 and 10 days post-excission. Following excission, the serum ganglioside sialic acid levels dropped from 50 ± 10 nmoles/ml to 20 ± 5 nmoles/ml and remained at this low level.

Human studies. Data with human subjects are shown in the following Table III:

TABLE III

Lipid-soluble sialic acid in sera of human carcinoma patients.

| Sex | Tumor status | Number of individuals | nanomoles sialic acid per ml serum ± standard dev. |
|---|---|---|---|
| Female | Normal* | 10 | 16 ± 3 |
|  | Mammary carcinoma | 7 | 49 ± 20 |
|  | Post-surgery** | 6 | 31 ± 8 |
|  | Colonic carcinoma | 5 | 49 ± 8 |
|  | Post-surgery** | 3 | 39 ± 1 |
| Male | Normal* | 8 | 24 ± 4 |
|  | Colonic carcinoma | 5 | 47 ± 9 |
|  | Post-surgery** | 3 | 24 ± 9 |

*Control values for pooled transfusion blood (4 different lots) were 20 ± 2 nanomoles sialic acid per ml serum.
**7–54 days Within the normal population, the variation was ± 20% which approximates the uncertainty of the extraction procedure coupled with that of the colorimetric method for determination of sialic acid. Sera from human males yielded somewhat higher values than from human females but the sample size is still too small to substantiate this trend. Values did not vary with age of the individual; a slight downward trend was noted. All subjects were human adults aged 21 to 71. As with the animal model, serum sialic acid of the glycolipid fraction was elevated nearly 2-fold in the carcinoma patients and appeared to decline post-surgery.

PREFERRED EMBODIMENT OF THE INVENTION

A viable organic matter sample such as sera or blood plasma (1.0 ml), fresh or frozen, with or without anticoagulant, in which sialic acid has not been destroyed is extracted with 10 volumes of chloroform-methanol (1:1) for 2 hrs after which 10 volumes of chloroform methanol (3:1) are added and the extraction continued for an additional 2 hrs. The extracts are filtered (e.g. through glass wool) and the residue is rinsed 3 times with 2 ml portions of chloroform-methanol 2:1. The combined filtrates are then concentrated by evaporation under nitrogen under reduced pressure and at ambient temperature or any other conditions well known to those in the art that lead to concentration of the extract without destruction of sialic acid. The extract is then resuspended with vigorous mixing in a total volume of 3 ml chloroform-methanol (2:1, by volume) so that a single phase is produced. To this treated filtrate, and for purposes of adjusting the ionic strength and pH of the sample are then added 100 microliters of a 0.1% solution of tripotassium citrate, followed by vigorous mixing and the resulting precipitate comprised of glycoproteins, proteolipids and other related materials is removed. Volumes of 1.0 ml (in duplicate) of the post-citrate supernatant thus obtained from the starting sample (sometimes referred to herein as the "soluble phase" of the sample which means all of the liquid that remains after the precipitate formed in the preceding step has been removed) are then evaporated to dryness thereby removing the organic solvents. The sample is then treated with 0.5 ml of 0.1 N hydrochloric acid and reacted for 1 hr at 80° C to free (hydrolyze) the lipid-bound sialic acid. To improve accuracy, a standard quantity of 25 nanomoles of sialic acid may be added to each sample. Free sialic acid is then determined by any standard procedure such as the one described by Warren, J. Biol. Chem., 234, 1971 (1959).

Clinicial test data show that, by using the following empirical formula:

$$3.1[90(\text{Absorbance}_{549 \text{ nanometers}}) - 33(\text{Absorbance}_{532 \text{ nanometers}})]$$

− 25 = nanomoles sialic acid/ml of serum and using the Warren method in combination with the above formula to correct for unspecific absorbance, normal values for humans are 16 ± 4 for females and 24 ± 8 for males. Values greater than 24 for human females and greater than 40 for human males indicate cancer.

It will be appreciated by those skilled in the art that obvious equivalents of the invention described may be practiced, and this invention is limited only by this entire disclosure and the scope of the appended claims.

We claim:

1. A method for detection of cancer comprising the steps of:
   extracting a viable organic matter sample taken from a test subject with an organic solvent to recover a reproducible fraction of lipid associated sialic acid;
   concentrating the extract obtained by the preceding step using conditions that minimize destruction of sialic acid;
   adding sufficient chloroform-methanol to form a single phase;
   adjusting the ionic strength and pH of the sample to remove glyco-proteins, proteolipids and other related materials by precipitation;
   removing the precipitates that resulted from the preceding step;
   drying the soluble phase of the sample whereby organic solvents are removed;
   hydrolyzing the dried soluble phase of the sample to free the bound sialic acid;
   determining the free sialic acid of the sample;
   correcting the determination of the preceding step empirically for unspecific absorbance due to residual lipids and other related materials; and
   comparing the sialic acid content per unit of the starting sample with comparable values for cancer free subjects whereby a predetermined elevation in sialic acid indicates cancer.

2. The method according to claim 1 in which the concentrated sample is treated with a chloroform-methanol mixture being approximately 2:1 by volume.

3. The method according to claim 1 in which the ionic strength and pH of the sample is adjusted by addition of a salt in a quantity sufficient (by empirical observation) to free glycolipid from bound forms and to precipitate out glycoproteins and proteolipids and other related materials.

4. The method according to claim 3 in which, for each 3 ml of chloroform-methanol of the sample, 100 microliters of a 0.1% solution of said salt is added.

5. The method according to claim 3 in which the salt is tripotassium citrate.

6. The method according to claim 3 in which the salt is potassium oxalate or sodium tartrate.

7. A method for cancer detection comprising:
   extracting a viable sample of blood sera or plasma in an amount of about 0.1 ml up to about 10 ml with about 10 volumes of chloroform-methanol (1:1, by volume) to form a single phase,
   the preceding extraction step being carried on with the final ratio of chloroform to methanol approximately 2:1, by volume until a reproducible fraction of the total lipid-bound sialic acid (normally greater than 90% of added monosialoganglioside $G_{m1}$) is extracted;
   removing the precipitate from said sample that is formed by the preceding step and retaining the soluble phase of said sample;
   washing the said precipitate with excess chloroform-methanol to remove residual glycolipids and combining these extracts with the said soluble phase of the sample;
   concentrating the said soluble phase into a dried sample by evaporation to remove water and then redissolving said dried sample in a volume of chloroform-methanol (2:1 by volume) about 3 times that of the volume of the said initial viable sample;
   adding, for each 3 ml of chloroform-methanol, 100 microliters of a solution of salt having an ionic strength and pH (determined empirically) sufficient to release bound glycolipids and to remove contaminating glycoproteins and proteolipids and related materials by precipitation;
   discarding the resulting precipitate;
   drying the soluble phase remaining of the sample to remove organic solvents;
   hydrolyzing the dryed soluble phase of said sample to free the bound sialic acid;
   determining free sialic acid of the sample by any standard procedure with predetermined corrections for unspecific absorbance due to residual lipids and other contaminants; and
   comparing the sialic acid content per unit of starting material with comparable values for cancer free subjects whereby a predetermined elevation in sialic acid indicates cancer.

8. A method for cancer detection comprising the steps of extracting a viable sample of sera or blood plasma, or tissue, with 10 volumes of chloroform-methanol (1:1 by volume) for about 2 hours;
   adding about 10 volumes of chloroform-methanol (3:1 by volume) and continuing the extraction for about 2 hours more;
   filtering the extracts thus obtained thereby obtaining a residue of said viable sample on the filter and a filtrate of said viable sample that passes through the filter;
   washing the said sample residue after filtration several times with 2 ml portions of chloroform-methanol (2:1 by volume);
   concentrating the sample filtrates by evaporation under nitrogen and resuspending said filtrates with vigorous mixing in a total volume of 3 ml chloroform-methanol (2:1 by volume) to reform a soluble phase of the said viable sample;
   treating said soluble phase of the sample by addition of 100 microliters of a 0.1% solution of salt characterized by its chemical activity which releases the bound glycolipids in said sample but does not precipitate them, said same salt also further acting to precipitate out glycoproteins and proteolipids and other related substances from said sample, to form a precipitate which is then removed and discarded;
   drying duplicate volumes of 1.0 ml of the remaining soluble phase of said sample;
   adding 0.5 ml of 0.1 N hydrochloric acid and reacting said resultant solution for about 1 hour at about 80° C;
   determining total free sialic acid in the remaining sample by any standard procedure, corrected for unspecific absorbance, whereby nanomoles sialic acid/ml of serum is calculated; and comparing the subject sample with a standard sample of a cancer free subject, a predetermined elevation in said nanomoles being indicative of cancer in the test subject.

9. The method according to claim 8 in which the salt is tripotassium citrate.

10. The method according to claim 8 in which the salt is potassium oxalate or sodium tartrate.

11. The method according to claim 8 in which a combination of salts is used, such combination being characterized by its chemical activity that releases the bound glycolipids in said sample but does not precipitate same, and further characterized by its chemical activity that precipitates out the glycoproteins from said sample.

* * * * *